(12) United States Patent
Caillouette

(10) Patent No.: US 7,503,899 B2
(45) Date of Patent: *Mar. 17, 2009

(54) DIGITAL TYPE COLOR COMPARISONS IN VAGINAL MOISTURE PH DETERMINATION

(75) Inventor: James C. Caillouette, Pasadena, CA (US)

(73) Assignee: Femtek LLC, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/584,821

(22) Filed: Oct. 24, 2006

(65) Prior Publication Data

US 2008/0009769 A1  Jan. 10, 2008

Related U.S. Application Data

(63) Continuation-in-part of application No. 11/235,741, filed on Sep. 26, 2005.

(51) Int. Cl.
 *A61B 5/00* (2006.01)
 *B65D 81/00* (2006.01)
(52) U.S. Cl. ...................... 600/573; 600/584
(58) Field of Classification Search .......... 600/562, 600/573, 584, 572
See application file for complete search history.

(56) References Cited

U.S. PATENT DOCUMENTS 5,710,372 A * 1/1998 Becket ................. 73/53.01
5,762,614 A    6/1998 Caillouette
5,782,801 A    7/1998 Caillouette
5,827,200 A    10/1998 Caillouette
5,916,176 A    6/1999 Caillouette
6,013,036 A    1/2000 Caillouette
6,019,734 A *  2/2000 Parkinson ............. 600/572
6,117,090 A    9/2000 Caillouette
6,390,991 B1   5/2002 Caillouette
6,406,441 B1   6/2002 Caillouette
6,544,196 B2   4/2003 Caillouette
6,673,630 B2 * 1/2004 Albarella et al. ........ 436/518

* cited by examiner

*Primary Examiner*—Max Hindenburg
*Assistant Examiner*—Jonathan M. Foreman
(74) *Attorney, Agent, or Firm*—William W. Haefliger

(57) ABSTRACT

Apparatus for quick screening for vaginal moisture pH level as related to a pre-selected pH level, comprising a manipulable element including a probe insertible into the vagina, at least one pH indicator on the element, the indicator characterized as producing a color which corresponds to pH level of vaginal moisture contacting the indicator, and a local comparison zone on the element having a color corresponding to a predetermined pH level, and positioned and shaped for quick color comparison with the color of the indicator after indicator contact with vaginal moisture. A test site for vaginosis may also be located on the probe, in non-interfering relation with said indicator and/or said zone.

24 Claims, 6 Drawing Sheets

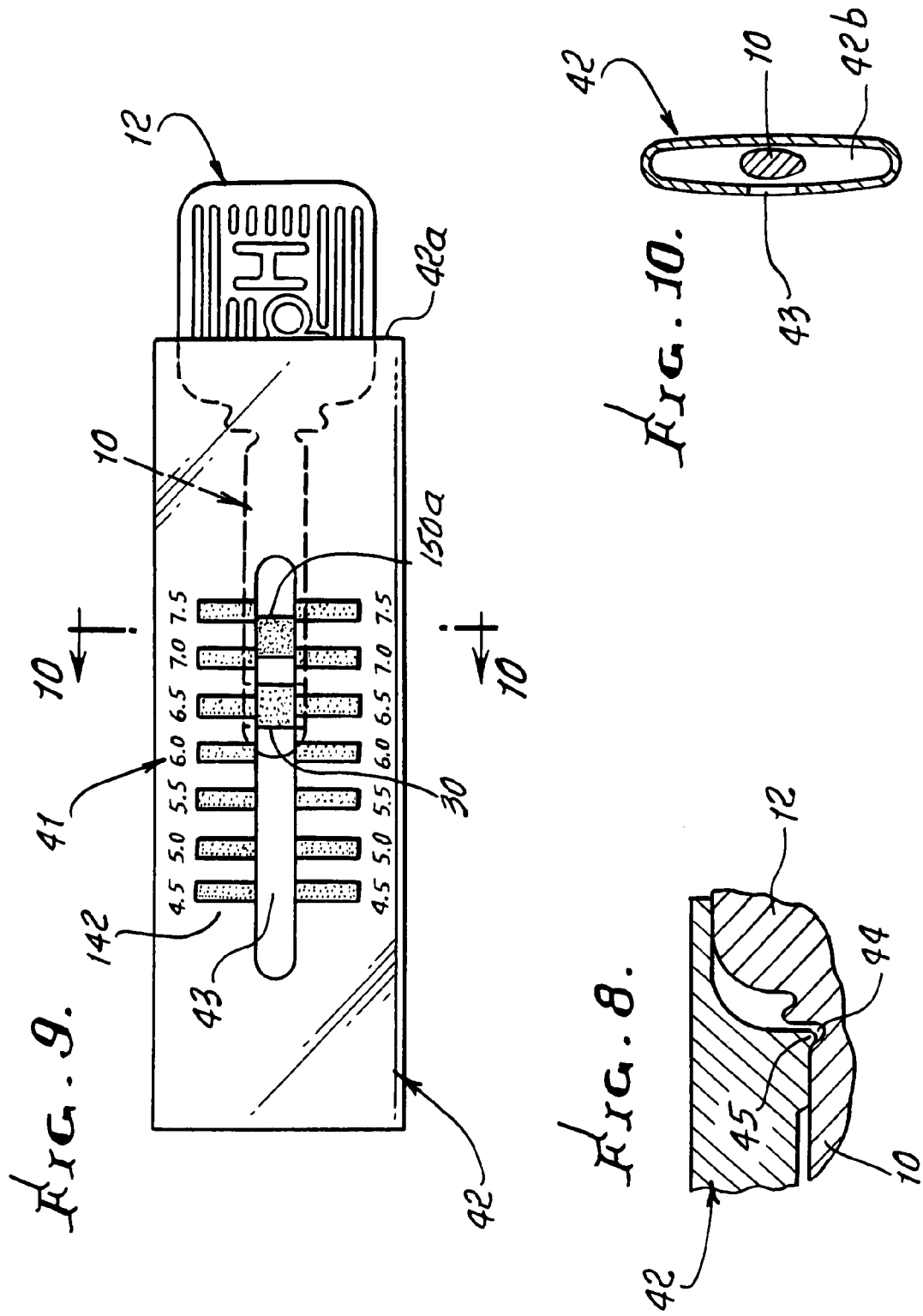

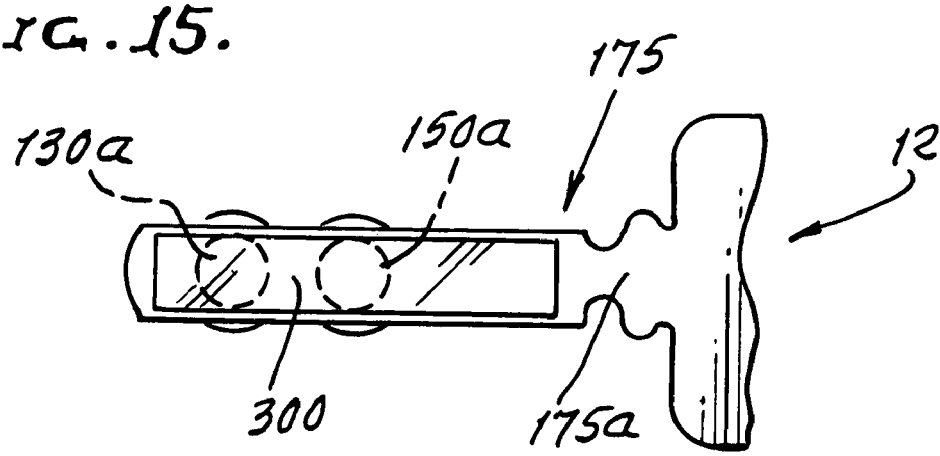
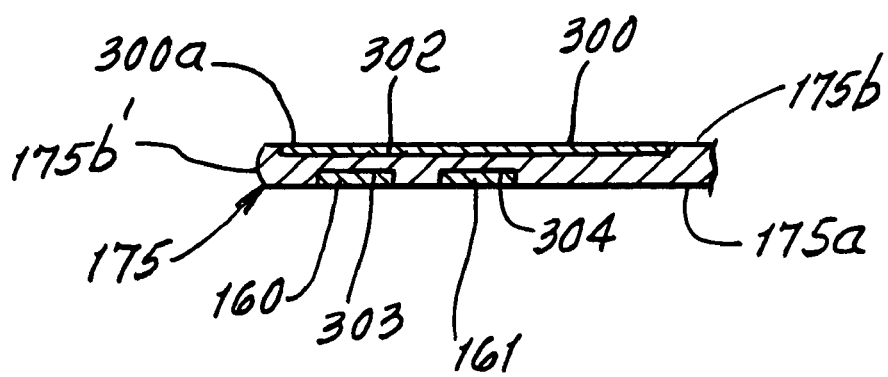
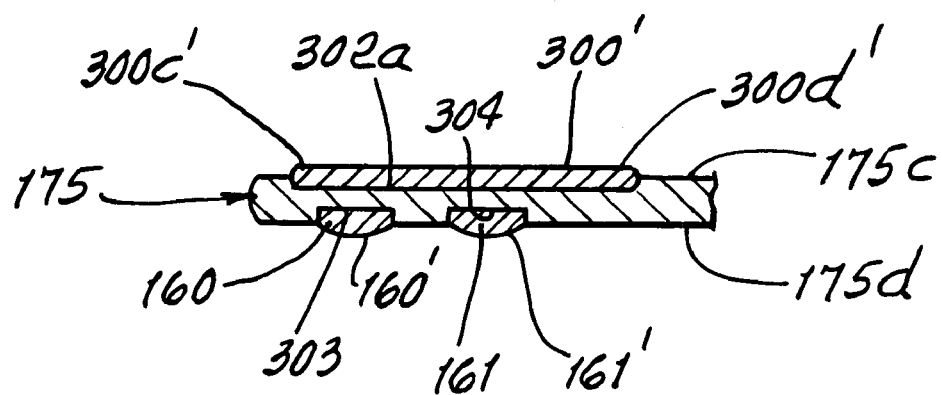

DIGITAL TYPE COLOR COMPARISONS IN VAGINAL MOISTURE PH DETERMINATION

This application is a continuation-in-part of pending U.S. application Ser. No. 11/235,741, filed Sep. 26, 2005.

BACKGROUND OF THE INVENTION

This invention relates generally to testing of body fluid, one example being pH measurement of body fluid, such as vaginal and/or urethral fluid, or moisture, and more particularly, to a rapid, easily performed method of such testing, or obtaining such measurement, as on a preliminary rapid basis.

There is continued need to obtain pH measurement of vaginal fluid, as for example in the determination of whether amniotic fluid has escaped into the vagina, during late pregnancy; another example is testing to determine need for estrogen therapy. There is also need for quick, simple test determination that positively alerts the user to possible problems indicated by a changed pH condition in the vagina with respect to a standard. Such a determination is a type of "digitally" quick determination.

SUMMARY OF THE INVENTION

It is a major object of the invention to provide an improved vaginal probe apparatus and quick test procedure which meets the above needs. Basically, the apparatus of the invention includes:

a) a manipulable element including a probe insertible into the vagina, b) a pH indicator on one side of the element, the indicator characterized as producing a color which corresponds to pH level of vaginal moisture contacting the indicator, c) and a second indicator on another side of said element, said second indicator being elongated lengthwise of the element and being an amine indicator.

Another object is to provide the second indicator of a length to extend in proximity to the probe tip, and to be incorporated on a strip adhered to the side of the probe opposite the first indicator.

Another object is to provide a local comparison zone exhibiting a color which corresponds to a fixed standard, such as a predetermined pH level. That zone may be on the probe proximate the pH indicator as for example in local and quick visual comparison proximity to the moisture responsive indicator. Both pH level and presence of amine are detected in one insertion usage of the device A further object is to provide both the pH indicator and the color comparison zone to have substantially the same sizes and shapes, for enhancement of screening visual accuracy of color comparison, especially when the color of the zone (standard) is close to the color of the indicator as driven by vaginal moisture pH.

Another object is to locate the comparison zone and pH indicator mutually lengthwise of the probe for enhancement of "digital", side-by-side recognition of any deviation or differences between the colors of these elements indicating possible physical problems. The comparison zone "standard" color may be located on the surface of a plastic component, in substantially planer alignment with the plane of the pH indicator surface. Also, the pH indicator is preferably located closer to the probe tip than the "standard" zone, to enable or facilitate subsequent color comparison in side-by-side relation with a pH color chart.

A yet further object is to provide a carrier for carrying the element, and a pH color chart associated with the carrier.

An added object is to provide a device and method for quick testing to determine vaginal pH and also to test for bacterial vaginosis.

The method of quick screening for vaginal moisture pH level as it relates to a pre-selected pH level, includes the steps:

a) providing a manually manipulable element including a probe insertible into the vagina, b) providing at least one pH indicator on that element, the indicator characterized as producing a color which corresponds to pH level of vaginal moisture contacting the indicator, c) and providing a local comparison zone on the element having a color corresponding to a predetermined pH level, and positioned and shaped relative to the pH indicator for quick color comparison with the color of that indicator after indicator contact with vaginal moisture.

That method may include the steps of contacting the indicator with vaginal moisture, and then visually comparing the color of said "standard" zone with the color of the indicator.

In these regards, the color comparison zone standard may have a color associated with pH level of about 4.5, and which does not vary with changes in pH level of moisture in contact with the zone.

Yet another object is to provide a method for testing for vaginal pH and for vaginosis, using a single probe element that includes the steps:

a) providing at least one pH indicator on the probe element said indicator characterized as producing a color which corresponds to the pH level of vaginal moisture contacting the indicator, b) and locating an elongated test site for vaginosis on the probe element in sufficiently spaced relation to the pH indicator, as for example on the reverse side of the probe, so that vaginal moisture at the test site for vaginosis will not come into contact with the pH indicator, during normal use of said method, and so that vaginal moisture will assuredly contact that test site. As will be seen the test site is preferably an elongated lengthwise extending strip that incorporates an hydroxide reactive with a vaginal bacterial produced amine. Alternatively, the probe element may have opposite end portions adapted to be separately inserted into the vagina, the pH indicator located at one end portion and the elongated test site for vaginosis located or terminating at the other end portion. A further object is to provide a probe element that has a mid-portion of a length adapted to be grasped by the user, for manipulating the probe to separately insert said opposite end portions into the vagina.

A yet further object is to provide a probe that has opposite sides, the pH indicator located at one of such sides, and the elongated test site for vaginosis located at the other of such opposite sides, to assuredly collect moisture for both pH level testing and amine presence testing, in one insertion usage of the device.

These and other objects and advantages of the invention, as well as the details of an illustrative embodiment, will be more fully understood from the following specification and drawings, in which:

DRAWING DESCRIPTION

FIG. 8 is a fragmentary view showing interlocking of the sheath and probe;

FIG. 9 is an enlarged view showing details of the sheath, with probe viewing window, and color comparison measurement zones, on the sheath; and also showing comparison of a color change of a test element with different colored zones on a sheath or other carrier;

FIG. 10 is a section taken on lines 10-10 of FIG. 9;

FIG. 15 is plan view of a probe side carrying an elongated strip to detect amine;

FIG. 16 is a section through a modified probe; and

FIG. 17 is a section through a further modified probe.

DETAILED DESCRIPTION

Figure 1:
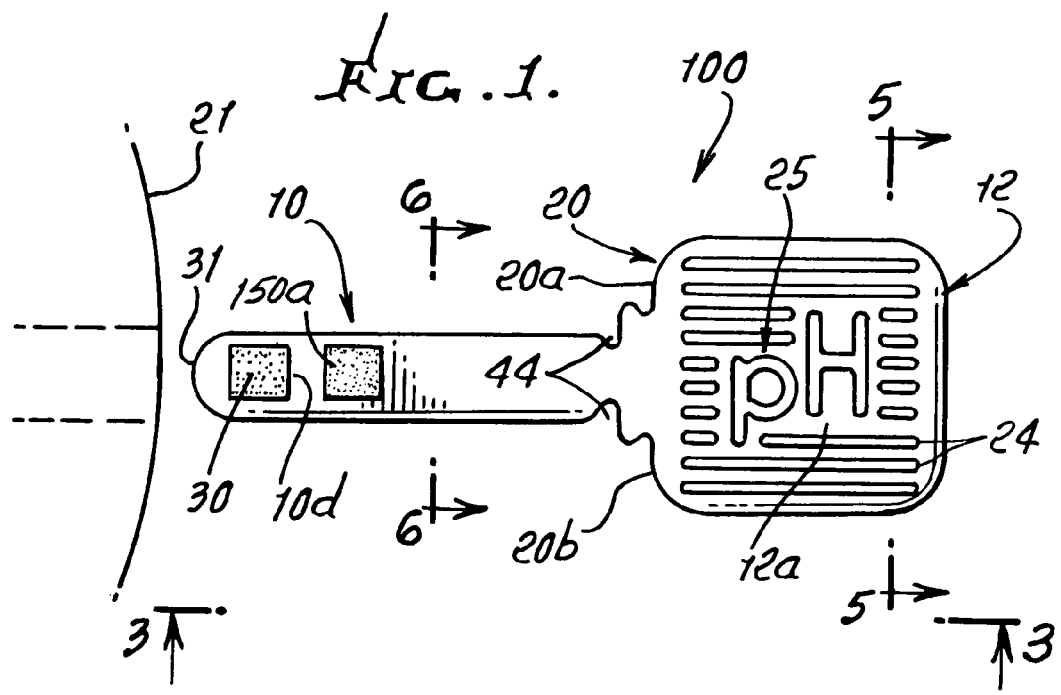
FIG. 1 is a top plan view of a probe and support incorporating the invention.
Figure 2:
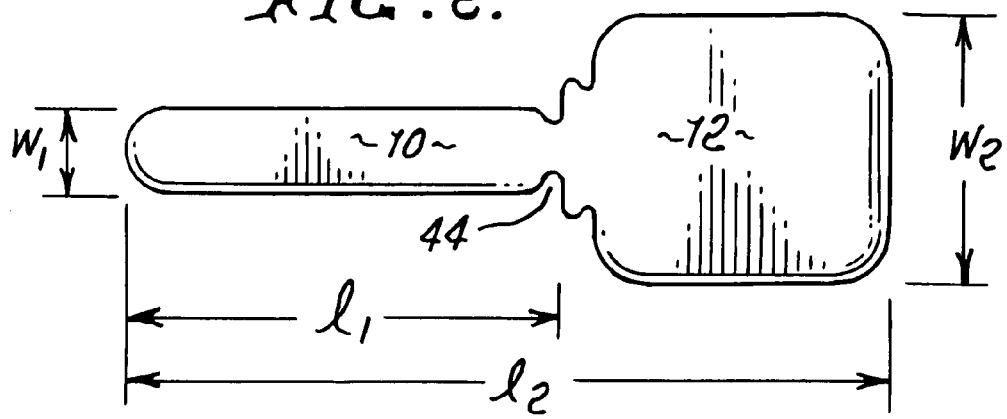
FIG. 2 is a bottom plan view of the FIG. 1 probe and support.

Referring first to FIG. 1, it shows a device that includes:

a) a longitudinally elongated probe insertible into the vagina, for a test purpose, b) a support operatively connected with the probe projecting away from the support, c) the support including:

i) a manually manipulable handle, ii) and an edge presented generally longitudinally for limiting probe insertion into the vagina.

Figure 3:
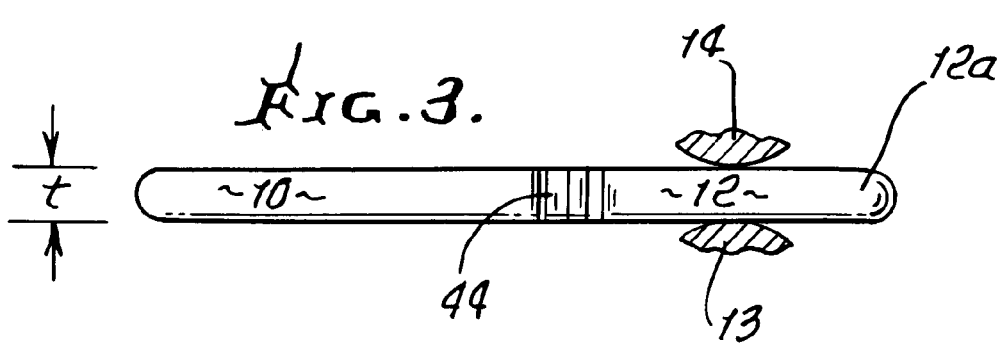
FIG. 3 is an edge view taken on lines 3-3 of FIG. 1.

As shown, the probe 10 of the apparatus 100 protrudes lengthwise from the support 12, which defines a handle 12a that can be easily gripped between the thumb 13 and forefinger 14 of the user, as seen in FIG. 3. The probe and support preferably have key-like configuration, as shown.

Forwardly or longitudinally presented edge 20 of the support limits insertion of the probe, as by engagement with the body 21, and dual edges may be provided as at 20a and 20b, at opposite lateral sides of the probe, for that purpose. The apparatus 100 may for example consist of plastic, metal or compressed fiber (example paper).

Surface irregularities may be provided on one laterally facing side of the support, and such irregularities are shown to extend longitudinally to be grasped by the thumb and prevent lateral slippage, relative to the user's thumb. The irregularities are shown in the form of protuberances 24 which are laterally spaced apart.

The probe and support, or handle may have the following dimensions for best results:

probe overall length "$l_1$"=1½ to 2½ inches probe width "$w_1$"=¼ to ½ inch support width $w_2$=¾ to 1½ inch thickness "t"=3/16 to 5/16 inch overall length $l_2$ of probe and support=3¼ to 3¾ inches.

Preferably, $l_1 \cong 2$ inches $w_1 \cong$ ⅜ inch $w_2 \cong 1$¼ inch t≅¼ inch $l_2 \cong 3$½ inch.

Figure 6:
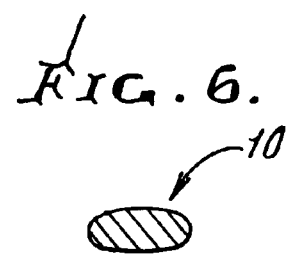
FIG. 6 is a section on line 6-6 of FIG. 1.

Also, the probe has an approximately flat, oval cross section, as seen in FIG. 6.

FIG. 1 also shows a test element or indicator 30 at the side of the probe, near its tip 31, to be pressed toward and against the vaginal wall. Element 30 typically comprises an indicator element, as for example one of the following:

i) a pH indicator ii) an amine indicator iii) a bacteria indicator iv) sialidase indicator v) prolidase indicator.

Figure 11:
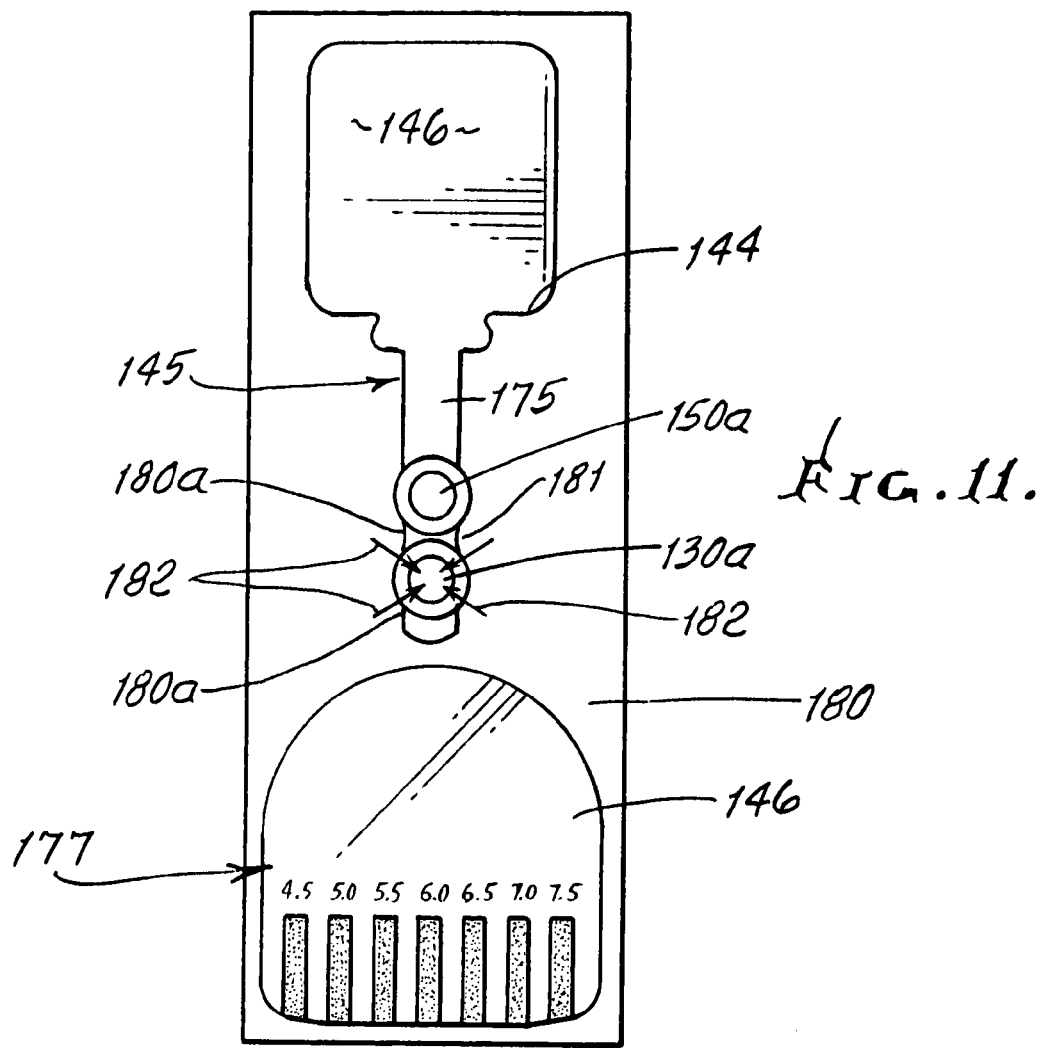
FIG. 11 is a side view of a preferred and modified apparatus.

The pH indicator or detector typically takes the form of a Nitrazine® strip or other carrier element adhered to the side of the probe, as for example by double sided adhesive tape. After exposure of the strip to vaginal moisture, its changed color (according to pH level) is compared with the series 41 of bands on a sheath 42, as seen in FIG. 9. Each band has a different color corresponding to a pH level color to which the detector strip may change. See for example the indicated pH levels 4.5, 5.0, 5.5, 6.0, 6.5, 7.0 and 7.5 adjacent the color bands. The bands may be provided on a support strip 142 adhered to the outer surface of the sleeve or receptacle 42. See also FIG. 11 showing a manipulable element 141 including a probe 143 and handle 144 received in recesses 144 in a plastic carrier 145, with support strip 146 adhered to the carrier. A series of bands 147, like bands 41, is located on the strip 146. Paper strips providing such elements are known, and sold under the name HYDRION papers, by Micro Essential Laboratory Inc., Brooklyn, N.Y. 11210. The band for pH 4.5 is typically bright yellow; the band for pH 6.0 is olive in color; and the band for pH 7.5 is navy blue.

Figure 4:
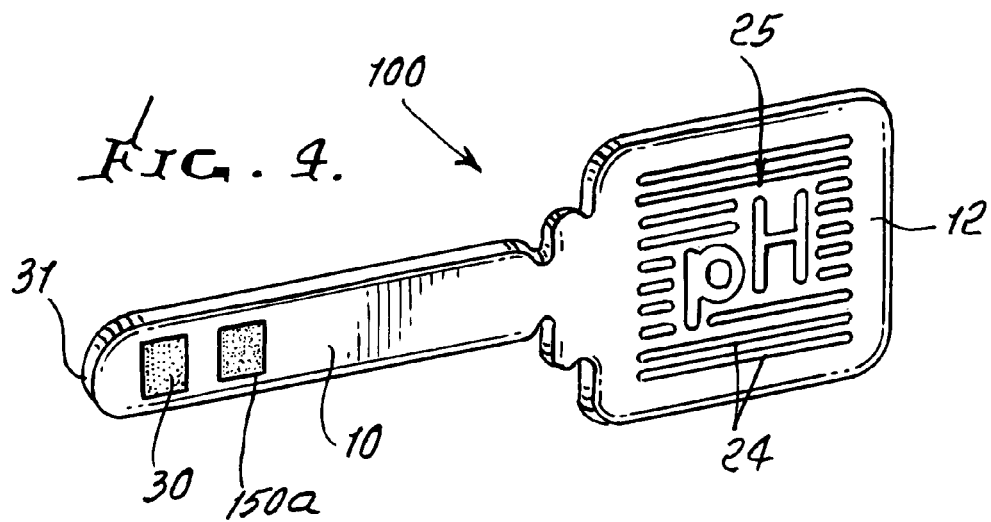
FIG. 4 is a perspective view of the FIG. 1 probe and support.
Figure 5:
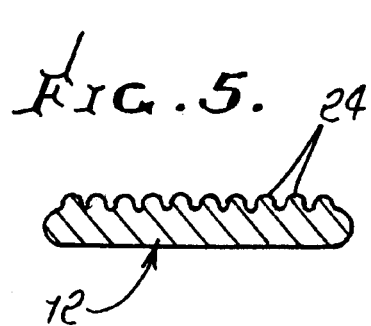
FIG. 5 is a section taken on lines 5-5 of FIG. 1.
Figure 7:
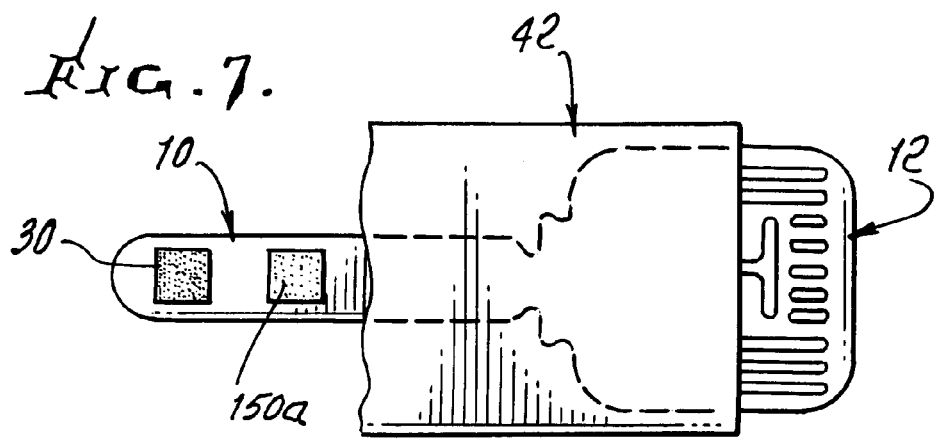
FIG. 7 is a view of the FIG. 1 probe received in a protective sheath.

In FIG. 11 a standard comparison zone is provided on the probe, one example being a plastic part 150 received in a recess 151 in the probe in proximity to the pH sensitive indicator 130. The outer surface of part 150 has a color corresponding to a predetermined pH level, at or near neutral pH level, such as 4.5 for example, for quick visual color comparison with the color of the indicator, after indicator contact with vaginal moisture. When a Nitrazine® indicator is used, the surface of part 150 can be sunflower yellow, to indicate a standard 4.5 pH. A corresponding part 150a is shown in FIGS. 1, 4 and 7.

In use, the user first visually compares the colors of the indicator (after exposure to vaginal moisture) and the standard zone (such as the surface of locality 150), and any difference in color indicates a possible problem. The color, size, and location of standard zone 150 are such as to provide prominent visual color comparison of zone 150 with the indicator. Next, the probe 10 and sleeve or receptacle 42 are relatively moved, lengthwise, to bring the detector strip 30 or indicator (after its exposure to moisture and color change as referred to above) into lateral registration with the color comparison bands, enabling ready visual comparison of the color of the detector strip with the closest color of one of the bands, enabling a pH level determination. For this purpose, a window zone 43 of the carrier sleeve adjacent the bands may be transparent to allow visual observation of the detector, through that zone, adjacent the bands. The entire sleeve and the strip 30 may be transparent.

In FIG. 11, the key-shaped plastic element 141, including probe 143 and handle 144 is removed from the carrier 145. The probe is inserted into the vagina to collect moisture and withdrawn, and the quick visual screen comparison is made, viewing the probe indictor and the standard comparison zone for quick detection of a possible problem, as for example need for estrogen. Thereafter, color comparison may be made with the colored bands, to more definitively determine moisture pH level. The probe is re-inserted into the elongated carrier receptacle 145.

The color changing reactant may consist, for example, of one or more of the following: Bromocresol Green, Bromocresol Purple, Nitrazine Yellow, Bromophenol Blue, and equivalents.

FIG. 9 also represents an optional confirmation step of obtaining a visual comparison of the color changed zone on the receiver 30 with a color, or different colors, or band color shades, where one color band may indicate presence of putrecine; another color band may indicate presence of cadaverine; and a third band may have another color or color shade close to but different from the first two, and so indicating absence of putrecine or cadaverine, or other bacterial producing amine, i.e. an amine test when compared side-by-side with the color on the receiver 30. Such amine indicates presence of pathogenic bacteria.

In FIG. 11, the indicator 130a and comparison zone 150a have substantially the same sizes and shapes, for enhancement of visual accuracy of color comparison. Also, the probe 145 has a substantially flat side 175, the indicator and comparison zones being exposed at that flat side. The local indicator and comparison zones are located in mutual proximity lengthwise of the probe, for rapid digital type color comparison readout (i.e. problem or no problem, per color visual differentiation). Both are substantially circular, and the exposed surfaces of each extend in substantially the same flat plane. Undulant edges 180a of the carrier and/or edges of 130a to 150a allow or facilitate relative travel of moisture along multiple paths 181 to reach the indicator 130a or zone 150a. See path arrows 182. The diameters of 130a and 150a may be between 3/16 and 3/8 inch, for optimum visual comparison effect. All of these contribute to enhancement of accurate, quick, viewing comparison to quickly detect color differences from a standard level. Carrier 180 receives the probe 145 and handle 146, and carries the pH color comparison chart 177.

Figure 12:
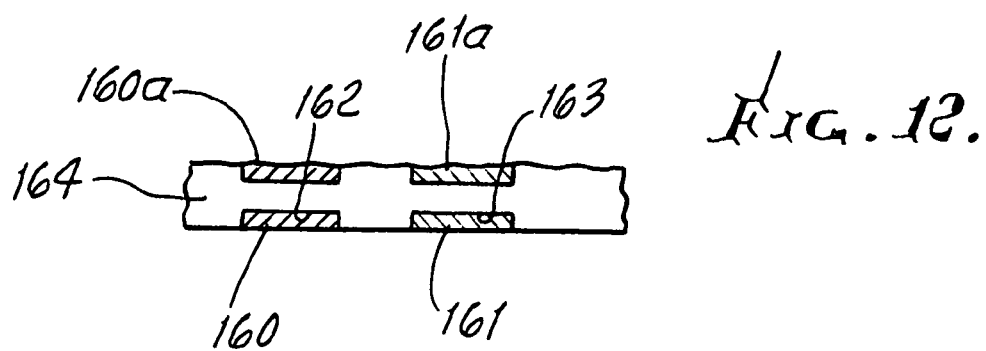
FIG. 12 is an enlarged view showing carrying on a probe of an indicator and comparison standard.

FIG. 12 shows reception of an indictor 160 and comparison zone plastic button 161, in recesses 162 and 163 in a probe 164, the outward facing surfaces of 160 and 161 being of generally the same size and shape and in the same plane for accuracy of comparison (equal illumination, light reflections, etc.).

Vaginal conditions related to pH are indicated as follows:

| 1. Bacterial Infection | above | 4.5-5.5 |
| 2. Menopause | above | 4.5-6.5 |
| 3. SPROM | above | 4.5-7.0 |
| 4. Osteoporosis | above | 4.5-6.5 |

Additional indicators and standard comparison zones may be provided on the probe, as shown at 160a and 161a, in FIG. 12, for redundancy and color differentiation confirmation.

U.S. Pat. No. 6,406,441 is incorporated herein, by reference.

Figure 13:
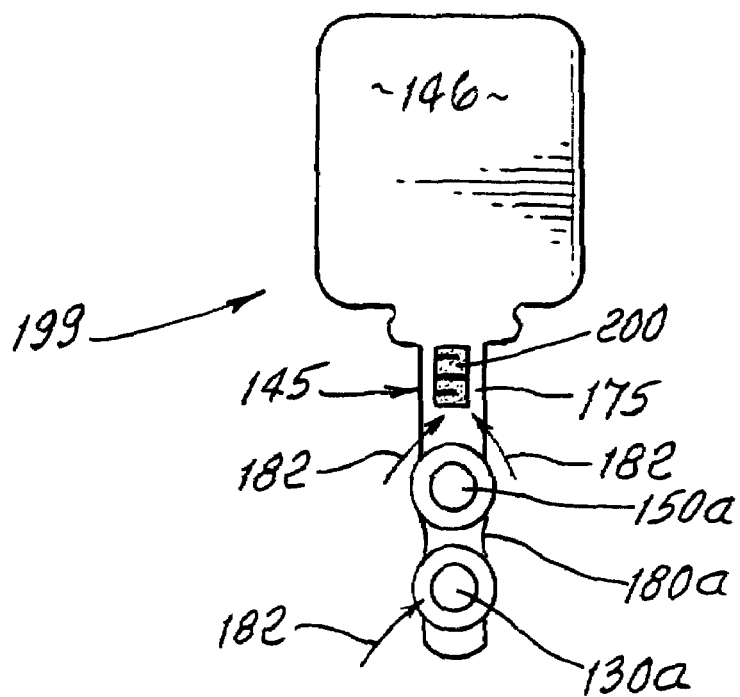
FIG. 13 is a view showing a vaginal probe with multiple test sites.

FIG. 13 shows a modification 199 in which elements the same as in FIG. 11 have the same identifying numerals. In addition, an elongated strip 200 is applied to the flat side 175 of the probe 145. Strip 200 includes, or carries, a thin layer of KOH, or other equivalent hydroxide reactive with an amine produced by vaginal bacteria, for use in testing for such an amine in the fluid sample from the vagina. See flow path arrow 182. When contacted with an amine in vaginal moisture the KOH reacts to produce a characteristic odor, which is a "fish" type odor, from which a doctor can diagnose the presence of amine in the test sample. Accordingly, the device 199 provides multiple test sites to enable quick multiple diagnostic tests for vaginal pH as may indicate estrogen deficiency as described, and for presence of amines (produced by vaginal bacteria) indicative of BV (i.e. bacterial vaginosis). Such amines include cadavarine and putrecine.

Figure 14:
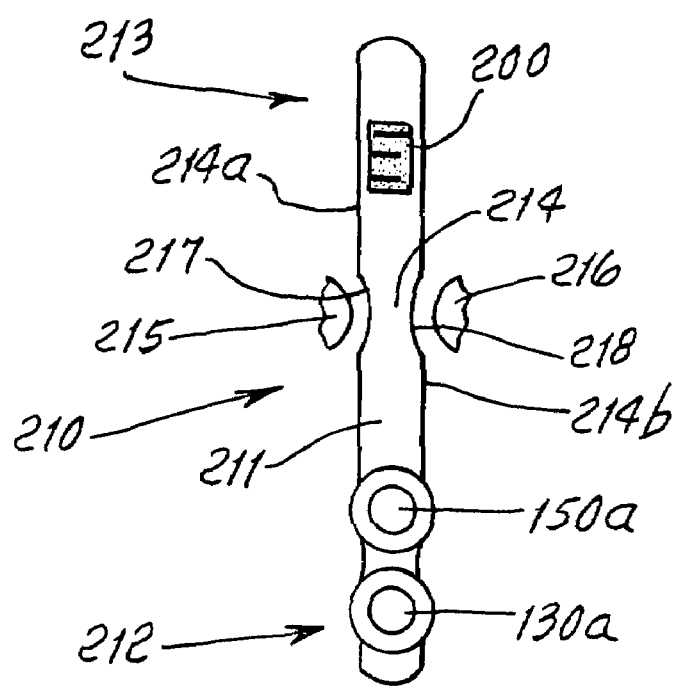
FIG. 14 shows another modification.

FIG. 14 shows a further modified device 210 which comprises an elongated thin stem 211 having test site zones 212 and 213 extending endwise oppositely of stem mid-portion 214. That mid-portion is adapted to be grasped as by the user's thumb 215 and first finger 216, during use of the device 210. There may be concave recesses 217 and 218 sunk in the edges 214a and 214b of stem mid-portion 214, for grasping and stem manipulation purposes. Test sites 130a and 150a at zone 212 are the same as provided in FIG. 13, i.e. have the same utility and relative placement.

Test site 200 has the same structure and utility as site 200 in FIG. 3; however, it is located at zone 213, remotely from sites 130a and 150a. In use the stem or stick is manipulated so that either zone 212 or zone 213 is first inserted into the vagina to receive vaginal moisture, and subsequently the stem is withdrawn and endwise removed so that the other of the zones 212 or 213 can then be separately inserted into the vagina to receive vaginal moisture and then withdrawn. This procedure avoids contact of moisture on site 200 with moisture on sites 130a and 150a, while still enabling rapid use and observation of all test sites 130a, 150a and 200. Such contact of moisture on site 200 with moisture on either or both of sites 130a and 150a could detrimentally change the pH at those latter sites due to the pH of the hydroxide containing moisture at site 200. As an alternative, the device of FIG. 13 could be modified to place site 200 at the opposite side of the stem 175, so that moisture on site 200 would be unlikely to be displaced as by smearing to contact moisture at sites 130a and 150a, at the opposite sides of the stem.

A protective film may be applied to cover site 200 until use, as for example by application to KOH or other hydroxide at the site of vaginal discharge, i.e applied for example by a Q-tip.

FIG. 15 is generally like FIG. 11, except the reverse side 175a of the probe is shown. An elongated strip 300 is adhered to flat side 175a strip 300 that includes or carries a thin layer of KOH, or other functionally equivalent hydroxide reactive with an amine produced by vaginal bacteria, for use in testing for such an amine in the fluid sample gathered from the vagina. Elongation of the strip, as for example to a length at least as long as ½ the probe length, (and typically at least 4 times the probe width) assures that vaginal moisture will be gathered at least one or more locations along the length of the strip, upon probe insertion into the vagina. When contacted with an amine in vaginal moisture, the KOH reacts to produce a characteristic odor, which is a "fish" type odor, from which a physician can diagnose the presence of an amine in the test sample. Such amines include cadaverine and putrecine.

FIG. 16 shows the elongated strip 300 received in an elongated shallow recess 302 sunk in probe flat side 175b, so that edges of the strip do not protrude to uncomfortably scrape against vaginal tissue. The forward end 300a of strip 300 extends in proximity to the probe tip 175b', to assure exposure of a substantial portion of strip 300 to moisture, despite possible shallow insertion of the probe 175 into the vagina. The pH indicator 160 and like comparison zone 161, as referred to above, are also sunk in recesses 303 and 304 and sunk in probe side 175a, for similar reasons.

In FIG. 17, the lower portion of modified elongated strip 300 is received into elongated shallow recess 302a. The upper portion of strip 300' protrudes above probe surface 175c, for enhanced assurance of contact with vaginal moisture; however, edges of the strip, such as forward edge 300c' and rearward edge 300d' are not sharp, i.e. are angled or blunted (for example rounded or beveled) to prevent scraping as referred to. See also the rounded outwardly exposed surfaces 160' of 160 and 161' of 161, at the opposite side 175d of the probe.

In each of FIGS. 15-17, the forward end of the amine indicator and the forward portion of the pH indicator are located close to the forward end of the probe to be assuredly exposed to moisture, despite shallow insertion of the probe into the vagina.

In FIGS. 11, 13 and 15 it will be noted that the pH indicator and the local comparison zone are linearly aligned in the direction of the probe, being aligned on a line which extends between two lateral edges of the handle presented toward the test sites, the pH indicator and the comparison zone both having curved edges facing oppositely and convexly away from that line, and protruding at opposite sides of the probe.

I claim:

1. Apparatus for quick screening for vaginal moisture pH level as related to a pre-selected pH level, comprising
    a) a manipulable generally key shaped element including a probe insertible into the vagina,
    b) a pH indicator on one side of said element, said indicator characterized as producing a color which corresponds to pH level of vaginal moisture contacting the indicator,
    c) and a second indicator on another side of said element, said second indicator being elongated lengthwise of the element and being an amine indicator,
    d) a local comparison zone having a fixed color corresponding to a predetermined pH level, and positioned and shaped for quick color comparison with the color of said pH indicator after pH indicator contact with vaginal moisture, said pH indicator having contact with vaginal moisture for visual comparison of the color of said zone with the color of said pH indicator,
    e) said pH indicator and said comparison zone spaced in mutual proximity on and lengthwise of the probe, and having like cross dimensions between $3/16$ and $3/8$ inch, and to have generally arcuate peripheral shapes,
    f) and wherein said element includes an enlarged substantially flat handle from which the probe projects longitudinally to be gripped between the user's thumb and forefinger, the handle having two laterally shaped edges presented toward said test site or sites and spaced generally longitudinally therefrom to limit probe longitudinal insertion into the vagina, said pH indicator and said local comparison zone being aligned on a line which extends between said two edges, and both having curved edges facing oppositely and convexly away from said line, and protruding at opposite edges of said probe.

2. The apparatus of claim 1 in which the indicators are on opposite sides, respectively, of the probe.

3. The apparatus of claim 1 wherein said element has a tip, and said second indicator extends lengthwise into proximity to the tip.

4. The apparatus of claim 1 wherein the second indicator has elongated strip form, and extends along the major length of said probe.

5. The apparatus of claim 1 wherein said pH indicator and comparison zone have substantially the same sizes and shapes, for enhancement of visual accuracy of color comparison.

6. The apparatus of claim 5 wherein said ph indicator and comparison zone are located lengthwise of the probe, for rapid digital type color comparison readout.

7. The apparatus of claim 1 wherein said probe has substantially flat opposite sides, said indicators being at said respective sides.

8. The apparatus of claim 1 wherein said pH indicator and comparison zone are located mutually lengthwise of the probe, for rapid digital response color comparison readout.

9. The apparatus of claim 8 wherein said pH indicator and comparison zone are both substantially circular.

10. The apparatus of claim 1 wherein said comparison zone includes the colored surface of a plastic part.

11. The apparatus of claim 10 wherein said plastic part colored surface and the observable surface of the pH indicator extend in substantially the same plane.

12. The apparatus of claim 1 including a carrier for carrying said element, and a pH color chart associated with the carrier.

13. The apparatus of claim 1 wherein one of said indicators includes a bacteria indicator.

14. The method of quickly screening for vaginal moisture pH level as it relates to a pre-selected pH level, that includes the steps:
    a) providing a manually manipulable generally key shaped element including a probe insertible into the vagina,
    b) providing a pH indicator on said element, said indicator characterized as producing a color which corresponds to pH level of vaginal moisture contacting the indicator,
    c) providing a second indicator on another side of said element, said second indicator being elongated lengthwise of the element and being an amine indicator,
    d) providing a local comparison zone having a fixed color corresponding to a predetermined pH level, and positioned and shaped for quick color comparison with the color of said pH indicator after indicator contact with vaginal moisture, and contacting said indicators with vaginal moisture, and then visually comparing the color of said zone with the color of said pH indicator,
    e) and providing said pH indicator and said comparison zone spaced in mutual proximity on and lengthwise of the probe, and having like cross dimensions between $3/16$ and $3/8$ inch, and having generally circular shapes,
    f) and wherein said element is provided to include an enlarged substantially flat handle from which the probe projects longitudinally to be gripped between the user's thumb and forefinger, the handle having two laterally shaped edges presented toward said test site or sites and spaced generally longitudinally therefrom to limit probe longitudinal insertion into the vagina, said pH indicator and said local comparison zone being aligned on a line which extends between said two edges, and both having curved edges facing oppositely and convexly away from said line, and protruding at opposite edges of said probe.

15. The method of claim 14 wherein said zone has a color associated with pH level of about 4.5.

16. The method of claim 14 including smell sensing for presence of amine at a location along the length of the elongated second indicator.

17. The method of claim 14 wherein the pH indicator and local comparison zone edges are undulant relative to the probe that facilitate moisture travel along multiple paths to reach the pH indicator and/or comparison zone.

18. The method of claim 14 including also providing a test site on the element which when exposed to vaginal moisture enables an indication of vaginosis.

19. The method of claim 18 wherein said pH indicator, said comparison zone, and said test site for vaginosis are arranged in mutual proximity and located lengthwise of the probe.

20. The method of claim 18 wherein said test site for vaginosis is located on the element in sufficiently spaced relation to the pH indicator so that vaginal moisture at the test site for vaginosis will not come into contact with the pH indicator, during normal use of said method.

21. The method of claim 14 wherein said second indicator is on a lengthwise extending strip that incorporates a hydroxide reactive with a vaginal bacterial produced amine.

22. The method of claim 21 wherein said test site for vaginosis is located on the element relatively remotely from the pH indicator.

23. The method of claim 14 wherein said probe has opposite sides, said pH indicator is located at one of said sides, and the second indicator is located at the other of said opposite sides.

24. The method of claim 23 wherein said second indicator is a lengthwise extending strip that incorporates a hydroxide reactive with a vaginal bacterial produced amine, said strip having a length which is at least 4 times the major width dimension of the probe.

* * * * *